United States Patent [19]

Kaplan et al.

[11] Patent Number: 4,981,985
[45] Date of Patent: Jan. 1, 1991

[54] SYNTHESIS OF PHOTOLABILE CHELATORS FOR MULTIVALENT CATIONS

[75] Inventors: Jack H. Kaplan, Bala Cynwyd; Graham C. R. Ellis-Davis, Philadelphia, both of Pa.

[73] Assignee: Trustees of the University of Pennsylvania, Philadelphia, Pa.

[21] Appl. No.: 110,932

[22] Filed: Oct. 20, 1987

[51] Int. Cl.$^5$ .............................................. C07F 13/00
[52] U.S. Cl. .................................... 556/50; 556/134; 556/148; 558/44; 562/435
[58] Field of Search .......................... 558/44; 562/435; 556/50, 134, 148

[56] References Cited

U.S. PATENT DOCUMENTS 4,689,432  8/1987  Tsien et al. ............................ 558/44

OTHER PUBLICATIONS

A. M. Gurney & H. A. Lester, *Light-Flash Physiology with Synthetic Photosensitive Compounds*, 67 (2) Physiological Reviews 583 (Apr. 1987).

Optical Methods in Cell Physiology, Chapter 19, "New Tetracarboxylate Chelators for Fluorescence Measurement and Photochemical Manipulation of Cytosolic Free Calcium Concentrations," R. Y. Tsien (1986).

A. M. Gurney, R. Y. Tsien, and H. A. Lester, *Activation of a Potassium Current by Rapid Photochemically Generated Step Increases of Intracellular Calcum in Rat Sympathetic Neurons*, 84 Proceedings of the National Academy of Sciences U.S.A. 3496 (May 1987).

J. L. Pinkus et al., "A Convenient Stereospecific Synthesis of Axial Amines in Some Steroidal, Decalyl, and Cyclohexyl Systems," 27 J. Org. Chem. 4356 (Dec. 1962).

M. Morad "Photoinactivation of Caged-Ca$^2$ shows that Extracellular Ca$^{2+}$ Blocks the Ca$^{2+}$ Channel in Myocardium at a Superficial Membrane Site", 76 Circulation IV—331 (1987).

M. Naebauer et al. "Rapid Block of Cardiac Calcium Channels and Tension Development Induced by Photorelease of Extracellular CA$^{2+}$ in Frog Heart," 53 Biophysical Journal (1988).

C. C. Ashley et al., "'Double Cage' Activation of Single Skinned Muscle Fibers From the Frog by the Simultaneous Release of ATP and Calcium from Caged-ATP and NITR-5," 53 Biophysical Journal (1988).

Y. E. Goldman et al., "Activation of Skeletal Muscle Fibers by Photolysis of DM-Nitrophen, a New Caged, Ca$^{2+}$", 53 Biophysical Journal (1988).

J. H. Kaplan et al., "Properties and Applications of DN-nitrophen, a New Caged-Ca$^{2+}$," 53 Biophysical Journal (1988).

Y. E. Goldman et al., "Laser Pulse Photolysis Studies of Skeletal Muscle Contraction," 53 Biophysical Journal (1988).

A. P. Somlyo et al., "Photochemical Analysis of the Latency Steps Between Activation and Contraction in Smooth Muscle," 53 Biophysical Journal (1988).

R. J. Barsotti et al., "Cardiac Muscle Activation by Laser-Induced Photolysis of NItr-5 (Caged-Ca$^{2+}$)," 53 Biophysical Journal (1988).

N. Fidler et al., "Rate of Ca$^{2+}$ Releases Following Laser Photolysis of a New Caged Ca$^{2+}$," 53 Biophysical Journal (1988).

*Primary Examiner*—Ferris H. Lander
*Attorney, Agent, or Firm*—Woodcock Washburn Kurtz Mackiewicz & Norris

[57] ABSTRACT

A method of synthesizing photolabile chelators as EDTA and EGTA derivatives to be used in caging multivalent cations is disclosed. The chelators chelate the cations forming non-biologically active compounds. The chelated compounds can then be localized in or near biological systems. Upon irradiation, the chelated compound cleaves with the subsequent cleaved remainders having a substantially lower affinity for the chelated cation. Large amounts of cation are thus rapidly released and the effect of such concentration jumps on the biological system can be accurately studied.

8 Claims, No Drawings

SYNTHESIS OF PHOTOLABILE CHELATORS FOR MULTIVALENT CATIONS

This invention was made with Government Support under grants awarded by the National Institutes of Health. The U.S. Government has certain rights in this invention.

BACKGROUND OF THE INVENTION

1. Field of the Invention

This invention relates to an improved method for chelating multivalent cations. More particularly, the invention relates to a method of synthesizing photolabile chelators for chelating multivalent cations to be used for rapid delivery of such cations within biologic systems.

2. Description of the Prior Art

Calcium plays an important role as a "secondary messenger" in a variety of physiological processes in the regulation of cellular $Ca^{2+}$ and it is central to the control of excitation-contraction coupling in muscle and of excitation-secretion coupling in many systems. In addition, magnesium is a necessary cofactor in ATP-dependent enzymatic processes including ion pumps, the myosin ATPase in muscle and a variety of kinases. It is also necessary in most processes where organo phosphates are enzymatic substrates. Therefore, the ability to regulate rapidly the concentration of the divalent cations of these metals for the quantitative study of the kinetics of such processes with minimal perturbation to the system is desirable.

One of the prime applications for optical indicators in the field of biology is a study of how calcium ions act as intracellular signals. As stated above, fluctuations in cytosolic free calcium concentrations $[Ca^{2+}]$ are hypothesized to be crucial in the triggering and control of a wide variety of cellular responses. To test such hypotheses, one would ideally verify first that, during a physiological response, the $[Ca^{2+}]$ does change with an amplitude and time course consistent with a triggering role. Assuming that a rise in $Ca^{2+}$ concentration is detected, another important test is to raise the cytosolic $[Ca^{2+}]$ by artificial experimental means and see whether or not the physiological response is elicited.

The responses to calcium and magnesium in biological systems are often very rapid. Therefore, in order to adequately study such systems and the affect of such elements on them, a quick delivery system is required. Traditional methods for raising the $Ca^{2+}$ concentration have included ionophore administration or direct microinjection or ionophoresis of $Ca^{2+}$. Each of these methods have their problems, however, the principal one being the inability to raise the $Ca^{2+}$ concentration as rapidly as is desired.

Recently, a new approach has developed that uses optical probes in reverse. In such a process, photochemically sensitive chelators directed to particular cations are synthesized. These chelators can then change irreversibly from high to low cation affinity upon illumination. Thus, light releases the "caged" cation and generates a jump in cation concentration. In general, such a method should be more controllable in amplitude, time course, and spatial extent than is currently achievable by other classical techniques. The chief advantage of this light flash technique is the speed of the photochemistry and the fact that it can be applied to organized systems, such as muscle fibers and membranes under electrophysiological investigation, that cannot be flowed.

Several caged compounds have been developed in the field of light flash physiology. A general overview of that field is provided in A.M. Gurney & H.A. Lester, *Light-flash Physiology With Synthetic Photosensitive Compounds*, 67(2) PHYSIOLOGICAL REVIEWS (April, 1987), incorporated herein by reference.

One general approach to the rapid release of physiologically significant organic molecules and cations is the "caging" of their active functionality using the photoremovable ortho-nitrobenzyl group. This approach has been utilized to cage ATP where a 2-nitrobenzyl ester of ATP releases ATP upon illumination.

Several variations on caged calcium chelators have also been developed. One example, referred to as nitr-2, is discussed 40 OPTICAL METHODS IN CELL PHYSIOLOGY, CHAPTER 19, "New Tetracarboxylate Chelators for Fluorescence Measurement and Photochemical Manipulation of Cytosolic Free Calcium," R.Y. Tsien (1986). Photolysis leads to the breakoff of MeOH, thereby decreasing the calcium binding affinity of the rest of the molecule and uncaging the $Ca^{2+}$.

Nitr-2 effects a change in its effective dissociation constant from near 170 $\mu$M to 7 $\mu$M upon irradiation. In other words, nitr-2 binds calcium approximately 41 times as strongly prior to irradiation. While this compound marks a significant step forward, the magnitude of the change in calcium binding affinity is not as great as would be preferred. Further, the quantum yield upon irradiation is in the neighborhood of only 0.03 to 0.1. In addition, because the drop in calcium affinity is only on the order of 41 times, not all of the calcium originally caged to the now-cleaved molecules is released. Some of it remains chelated to the cleaved molecules. Thus, only a small amount of the caged calcium is released at any given time during irradiation. Even nitr-5, a revised version of nitr-2 referred to in the PHYSIOLOGICAL REVIEWS article cited above suffers from the same limitation on the change in calcium binding affinity. Still further, these prior art compounds are not suitable for caging other cations such, as $Mg^{2+}$, that are of significant interest to biological researchers.

Accordingly, there exists a need for a photolabile chelator capable of caging multivalent cations and thereafter releasing large amounts of such multivalent cations upon irradiation.

SUMMARY OF THE INVENTION

The present invention is directed to photolabile chelators used first to cage multivalent cations and then to release such multivalent cations when exposed to light. More particularly, o-nitrophenyl substituted derivatives of EDTA and EGTA serve initially as chelators having high affinities for divalent cations such as $Ca^{2+}$ and $Mg^{2+}$. The chelated or "caged" divalent cations are thereafter rapidly released at a desired location upon specific chemical transformation brought about by photochemical irradiation. The basis for the rapid release of the divalent cations, and the resulting step function increase in cation concentration, is the great difference in cation affinity between the tetracarboxylate chelators and the diacetic acid products.

The rapid release of such cations as $Ca^{2+}$ and $Mg^{2+}$, as disclosed herein, provides a mechanism that can be easily used within intact physiological systems to quantitatively study the kinetics of cation use within those systems.

Accordingly, it is an object of the present invention to provide a method for rapidly delivering significant amounts of multivalent cations to chosen locations within physiological systems with minimum perturbation to those systems. An advantage of the present invention is that concentration-jump experiments involving cations of biological interest can be performed near or within the specific cell or system desired to be studied. Other and further objects and advantages will appear hereinafter.

which would, upon specific chemical transformation in the form of chemical irradiation, allow the rapid release of the bound species. A generalized scheme for each can be represented as follows:

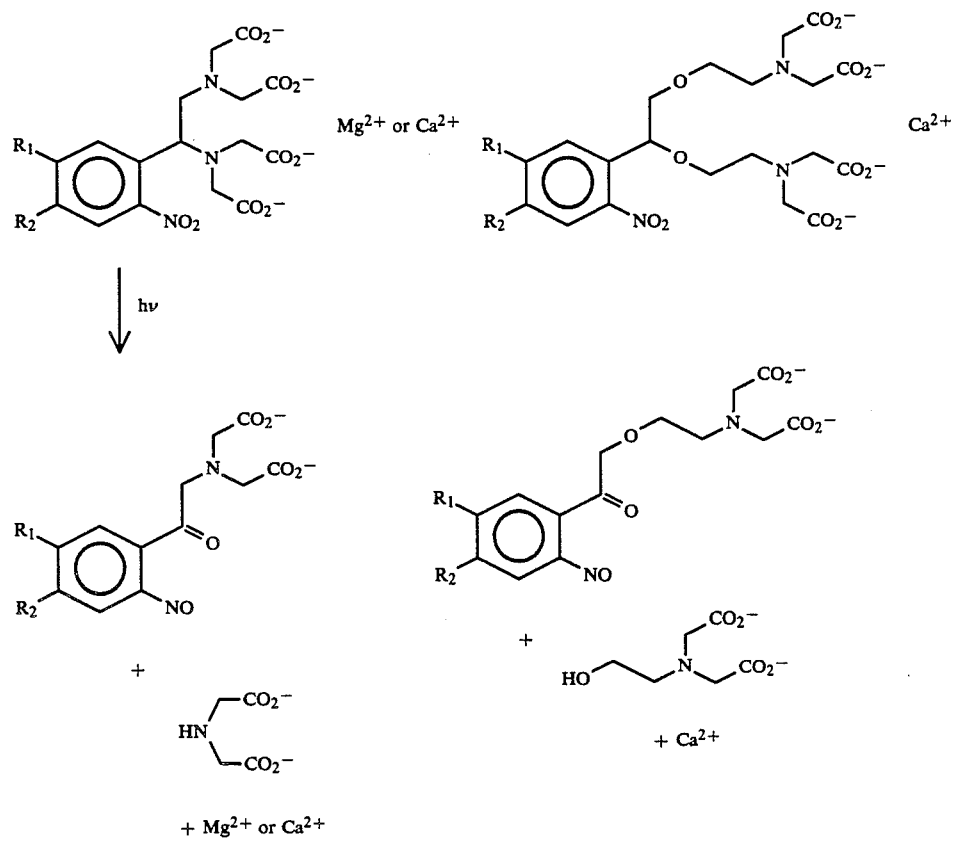

DETAILED DESCRIPTION OF THE PREFERRED EMBODIMENTS

One could imagine a generalized way of performing light flash studies wherein a physiologically important but photostable molecule would be placed within a universal photosensitive molecular cage and then be introduced near or within the biological system of interest before a light flash would liberate the molecule. Such a universal molecular cage, however, does not exist. As a result, special photosensitive molecules have to be designed for each application.

Both calcium and magnesium play important roles in cellular physiology. Furthermore, the biological processes using such elements proceed at a very rapid rate. Therefore, the method and product of the present invention are designed to allow the localized rapid increase in calcium or magnesium concentration needed to adequately study such biological systems. The intracellular calcium or magnesium concentration can be directly manipulated on a time scale of microseconds.

It was envisioned that o-nitrophenyl substituted derivatives of EDTA and EGTA would serve initially as chelators having high affinities for divalent cations, The basis for the increase in, for example, the calcium ion concentration is the substantial difference in affinity in the tetracarboxylate chelators and the diacetic acid products. Depending upon the starting material chosen to cage a particular cation, the dissociation constant, $K_d$, will vary from $10^{-8}$ M to $10^{-5}$ M at neutral pH. The diacetic acid products, on the other hand, will all end up with a dissociation constant of approximately $10^{-3}$ M. Thus, the caged cation becomes anywhere from $10^2$ to $10^5$ times less bound once the chelated compound is irradiated. As a result of this significant drop in affinity, a large portion of the previously caged cation splits from the original complex and becomes available in ionic form for reaction and use within the particular biological system being examined or treated.

The change resulting from the photochemical irradiation causes the chelated compound to split on a millisecond time frame, a big improvement over normal methods known in the art.

It should be noted that, while the ions of most importance at the present time are $Ca^{2+}$ and $Mg^{2+}$ and that the present invention is described in terms of those cations, the method of the present invention can be used with any multivalent cation that might be chelated by an EDTA or EGTA derivative. In particular, ions of zinc, cadmium, manganese, and iron could be used.

Once caged, the ion to be studied can be injected or otherwise placed near or in the particular biological system to be studied without immediate chemical reaction. EDTA and EGTA are stable calcium and magnesium binders that are not photosensitive. The substitution of an o-nitrophenyl group imparts the photosensitivity. The chelated compounds, however, appear biologically stable and will not react during the location process. Further, the cleaved molecules appearing after irradiation and releasing the caged cation are also biologically stable and will ultimately be taken up and removed by normal biologic methods.

Any suitable source of ultraviolet light can be used to irradiate the chelated compound and release the caged cation. The light can be either in flash form or continuous irradiation. For the particular chelated compounds disclosed herein, a light source irradiating above about 250 NM is effective to cleave the molecules. The upper limit of the light's wavelength will depend upon the particular compounds involved with approximately 500 NM being a normal upper limit. In a preferred embodiment, light of about 325–375 NM is used. In a more preferred embodiment, light of about 350 NM is employed. It should be noted that while light in the range below 280 NM might be effective to cleave the molecule, it would have a detrimental effect upon the biological specimen and is, therefore, not preferred.

The typical quantum yield of cleaved molecules obtained using the chelated compounds of the present invention exceeds 18% and is more commonly in the range of 20%. Due to the large drop in cation affinity, virtually all of the cation originally caged to the now-cleaved molecules is released. This substantial yield is one of the advantages over the chelating compounds disclosed in the prior art. Of course, upon continuous or subsequent exposure to irradiation, the overall yield will increase.

As can be seen from the scheme set forth above, the nitrophenyl substituant can be substituted at either the fourth or fifth carbon, or both. While the examples discussed below involve the use of a dimethoxy nitrophenyl, $R_1$ and $R_2$ can each be chosen from a group consisting of hydrogen, methoxy, halogen, methyl, hydroxy, carboxy, benzyloxy, carboxymethyl, vinyl, nitro, amino, dimethylamine, and thioalkyl, depending upon the starting materials available.

Preferable methods for preparing the chelating compounds to be used in caging the multivalent cation have also been discovered. While the chelated compounds of the present invention are not intended to be limited to those prepared specifically by the processes discussed below, these examples serve to show particular embodiments of methods for caging calcium or magnesium ions. Therefore, the following examples are set forth for illustrative purposes only and are not intended to limit in any way the scope of the invention disclosed and claimed herein.

EXAMPLE 1

1. A magnetically stirred suspension of methyl triphenylphosphonium bromide (22.02 g, 61.6 mmol) in dry tetrahydrofuran (THF) at 0° C. under $N_2$ was treated with 1M sodium hexamethyldisilizide in the same solvent (61.6 ml, 61.6 mmol). The resulting mixture was stirred at 0° C. for one hour. Thereafter, a solution of O-nitroveratraldehyde (10.0 g, 47.4 mmol) in dry THF was added by canullation and stirring was continued for an additional 18 hours at room temperature. A solution of saturated $NH_4Cl$ (200 ml) was added and the product was extracted with $CH_2Cl_2$ (3×150 ml), dried, and concentrated. Flash chromatographic purification of the residue on silica gel (elution with 25% ethyl acetate in hexanes) furnished 8.13 g (82% yield) of a styrene (2-nitro-4,5-dimethoxystyrene) of the structure (where Me represents a methyl group):

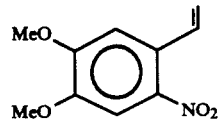

2. Osmium tetroxide (0.0457 mg, 0.18 mmol) in tertiary-butanol (2.34 ml) and 4-methylmoroholine-N-oxide (2.35 g, 20.0 mmol) as an 80% solution in $H_2O$ was added to a magnetically stirred solution of the styrene of step 1 (3.8 g, 18.2 mmol). The reaction mixture was stirred at room temperature for 45 hours, concentrated in vacuo, and purified by flash chromatography on silica gel (elution with ethyl acetate) to give 4.00 g (90% yield) of a diol, 1-(2'-nitro-4',5'-dimethoxyphenyl)-ethane-1,2-diol, of the form (0.175 g, 0.837 mmol of starting material was recovered—the yield was thus 95% based on consumed starting material):

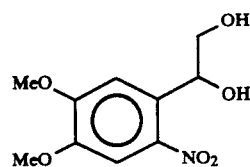

3. A mixture of the diol of step 2 (1.0 g, 4.11 mmol) and di-n-butyltinoxide (1.075 g, 4.32 mmol) was azeotroped with toluene. The suspension was concentrated in vacuo. Thereafter, dry methanol (30 ml) was added and the solution was refluxed under $N_2$ for two hours. The solution was concentrated and tetra-n-butylammonium iodide (3.4 g, 4.11 mmol), dry allyl iodide (1.38 g, 16.2 mmol), and dry toluene were added. This reaction mixture was refluxed for 22 hours, diluted with $H_2O$ (50 ml), and extracted with ethyl acetate (3×75 ml). The combined organic layers were dried, concentrated, and the residue subjected to flash chromatography on silica gel (elution with 50% ethyl acetate in hexanes) to give 0.200 g (20% yield) of recovered starting material and 0.889 g (80% yield) monoallyl ether (100% based on recovered starting material). A solution of the monoallyl ether (0.889 g, 3.29 mmol) and dry allyl bromide (1.40 g, 11.6 mmol) in dry dimethoxyethylene (DME) (10 ml) at 0 C was added to a stirred suspension of NaH (0.10 g, 4.17 mmol) in dry DME (10 ml) under $N_2$. The reaction mixture was stirred for 1 hour at room temperature, $H_2O$ (50 ml) was added, and the mixture extracted with ethyl acetate (3×50 ml). The combined organic layers were dried, concentrated and subjected to flash chromatography on silica gel (elution with 50% ethyl acetate in hexanes) to give 0.796 g (75% yield) of a diallyl ether (4-(2'-nitro-4', 5'-dimethoxyphenyl)-1,4-bis(allyl)ethyleneglycol) of the structure:

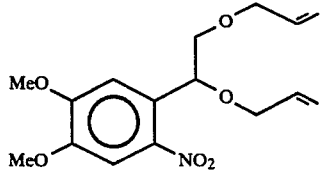

4. Ozone was bubbled through a cold (−78° C.), magnetically stirred solution of the diallyl ether of step 3 (0.783 g, 2.43 mmol) in CH$_2$Cl$_2$ (30 ml) until the solution was blue. Solvent evaporation left a residue that was taken up in methanol (40 ml). NaBH$_4$ (0.55 g, 12.2 mmol) was added to the magnetically stirred solution at 0° C. The reaction mixture was stirred for a further 18 hours at room temperature, saturated NH$_4$Cl solution (20 ml) was added, and the product was extracted with CHCl$_3$ (3 x 100ml). The combined organic were dried, concentrated in vacuo, and purified by flash chromatography on silica gel (elution with 10% methanol in ethyl acetate) to give 0.523 g (65% yield) of 4-(2′-nitro-4′,5′-dimethoxyphenyl-triethylene glycol. Triphenyl phosphine (0.700 g, 2.66 mmol), imidazole (0.180 g, 2.66 mmol), and iodine (0.500 g, 1.99 mmol) were added to a magnetically stirred solution in toluene (20ml) of the diol (0.110 g, 0.332 mmol). The reaction mixture was stirred at room temperature for 0.5 hours, saturated NaHCO$_3$ (20 ml) was added and the reaction mixture was stirred for a further 5 minutes. Then, enough I$_2$ was added to color the organic phase and the reaction mixture was stirred for a further 10 minutes. The reaction mixture was diluted with H$_2$O (50 ml) and extracted with CH$_2$Cl$_2$ (3×75 ml). The combined organic layers were dried, concentrated in vacuo, and purified by flash chromatography on silica gel (elution with 10% ethyl acetate in hexanes) to give 0.155 g (91% yield) of a diiodide (1-(2′-nitro-4′,5′-dimethoxyphenyl)-1, 2-bis(iodoethoxylethane) of the form:

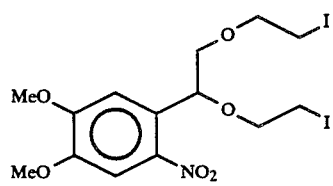

5. To a magnetically stirred suspension of iminodiacetic acid (50 g, 0.376 mol) in absolute ethanol (1000 ml) under N$_2$ was added boron trifluoride etherate (100 g, 1.127 mmol). The reaction mixture was refluxed for 3 days and concentrated in vacuo to a volume of 150 ml. A saturated NH$_4$Cl solution (500 ml) was added and the reaction mixture was extracted with CH$_2$Cl$_2$ (3×250 ml). The combined organic layers were dried and concentrated in vacuo. The crude product was distilled at 10 mm Hg to give 65.2 g (92% yield) of iminodiacetic acid, diethyl ester as a colorless liquid.

6. A solution of the diiode of step 4 (0.166 g, 0.301 mmol) in the iminodiacetic acid, diethyl ester (0.285g, 1.505 mmol) of step 5 was subjected to a pressure of 5000 psi for eight days. Flash chromatographic purification (elution with 15% hexanes in ethyl acetate) gave 0.136 g (65% yield) of an EGTA analog, 7-(2′-nitro-4′,5′-dimethoxyphenyl)-3,12-bis (carboxymethyl)-6,9-dioxa-3,12-diazatetradecanoic acid tetraethyl ester, having the structure (where Et represents an ethylene group):

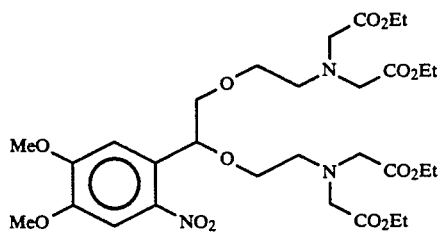

along with unreacted secondary amine.

7. The hydrolyzed EGTA analog of step 6 is then added to a solution containing free Ca$^{2+}$ to chelate with the Ca$^{2+}$ to form a chelated compound of the structure:

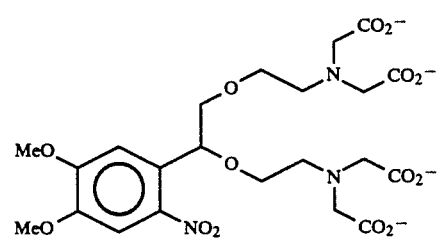

EXAMPLE 2

1. Step 1 of Example 1 was repeated to obtain 2-Nitro-4, 5-dimethoxystyrene.

2. Bromine (6.39 g, 0.040 mmol) was added to a cold (0° C.), magnetically stirred solution of the styrene of step 1 (8.13 g, 38.9 mmol) in CH$_2$Cl$_2$ (150 ml). The reaction mixture was extracted with a saturated Na$_2$SO$_3$ solution (100 ml) and the organic phase was dried and concentrated in vacuo to give 14.35 g (100% yield) of a dibromide (1-2′-nitro-4′,5′-dimethoxyphenyl)-ethane-1,2-dibromide) of the form:

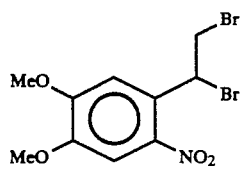

3. A solution of the dibromide of step 2 (1.37 g, 3.72 mmol) in iminodiacetic acid, diethyl ester (3.52 g, 18.6 mmol-prepared as in step 5 of the previous example) was subjected to 5000 psi for 21 days. Flash chromatographic purification on silica gel (elution with 30% ethyl acetate in hexanes) gave 0.980 g (44% yield) of an EDTA analog tetraester, 1-(2′-nitro-4′,5′-dimethoxyphenyl)-N,N′-1,2-ethane [N-(carboxylmethylglycine], having the structure:

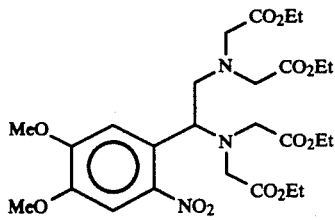

4. The hydrolyzed EDTA analog tetraester of step 3 is then added
to a solution containing free Mg2+to chelate with the Mg$^{2+}$to form a chelated compound of the structure:

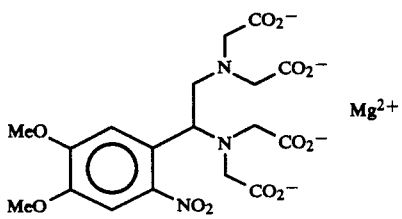

While several of the individual steps disclosed in the examples above might appear to be known to those in the art, the combined processes used to synthesize the chelated compounds is new. In particular, it is believed that the step of using high pressure chemistry to effect the alkylation of a secondary amine is unknown. While a pressure of 5000 psi was used, a lower pressure can be used. Lower pressures will slow results, however, and eventually a threshold pressure will be reached below which the alkylation will not proceed. On the other hand, higher pressures will facilitate the reaction.

It should also be clear that many of the particular parameters chosen for the examples above, e.g., measured amounts, temperatures, time periods, etc., are not necessary to achieve the desired results. In addition, particular variations of synthesis steps would also be apparent to those of ordinary skill in the relevant field.

The chelated compounds of the present invention can be used in an aqueous solution since they are generally hydrophilic. Further, while the chelated compounds currently being analyzed remain in liquid form, they can be manufactured in solid form as well.

In addition, while each of the variety of EDTA and EGTA derivatives will chelate to some extent with multivalent cations, there is some variation in the strength of the chelated bonding. For example, the EGTA dimethoxy derivatives do not perform as well with magnesium ions as they do with calcium ions. The EDTA dimethoxy derivatives, on the other hand, perform well with either ion. Much of these variations stem from the orientation of the particular compound's electron cloud and the effect of the cleaving of the molecule on the consequent orientation of the electron clouds of the remaining molecules. The shifting orientation is one of the major determinants of the affinity of the particular molecule for the relevant cation.

Thus, a method of producing photolabile chelators for chelating multivalent cations to thereby be used for the rapid release of cations within biological systems is disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A solution comprising photolabile chelator consisting essentially of one or more anions having the following structure:

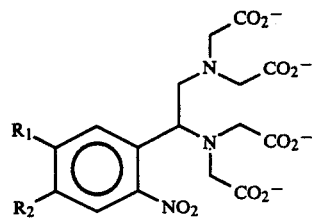

wherein $R_1$ and $R_2$ are each chosen from the group consisting of hydrogen, methoxy, halogen, methyl, hydroxy, carboxy, benzyloxy, carboxymethyl, vinyl, nitro, amino, dimethylamine, and thioalkyl.

2. A chelated compound comprising the photolabile chelator of claim 1 chelated with a multivalent cation.

3. The chelated compound of claim 2 wherein the multivalent cation is chosen from the group consisting of calcium, magnesium, zinc, cadmium, manganese, or iron.

4. The chelated compound of claim 2 wherein light in the range of 250-500 NM causes the photolabile chelator to split and form compounds having the following two structures:

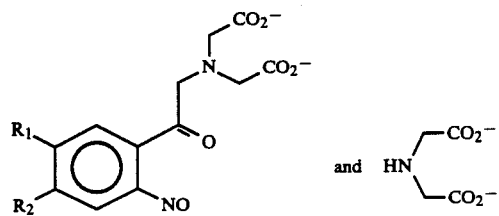

5. A photolabile chelator consisting essentially of anion having the following structure:

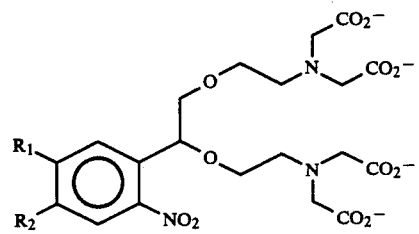

wherein $R_1$ and $R_2$ are each chosen from the group consisting of hydrogen, methoxy, halogen, methyl, hydroxy, carboxy, benzyloxy, carboxymethyl, vinyl, nitro, amino, dimethylamine, and thioalkyl.

6. A chelated compound comprising the photolabile chelator of claim 5 chelated with a multivalent cation.

7. The chelated compound of claim 6 wherein the multivalent cation is chosen from the group consisting of calcium, magnesium, zinc, cadmium, manganese, or iron.

8. The chelated compound of claim 6 wherein light in the range of 250-500 NM causes the photolabile chelator to split and form compounds comprising the following two structures:
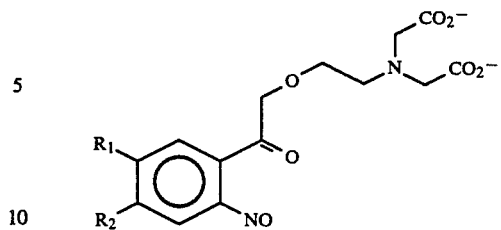
with a resultant decrease in cation affinity.

UNITED STATES PATENT AND TRADEMARK OFFICE
CERTIFICATE OF CORRECTION

PATENT NO. : 4,981,985
DATED : January 1, 1991
INVENTOR(S) : Kaplan et al.

It is certified that error appears in the above-identified patent and that said Letters Patent is hereby corrected as shown below:

Column 2, Line 42, replace "cations such," with
--cations, such--.

Column 4, Chemical Structure, insert the following symbols below the top right structure:

$\downarrow h\nu$

Column 8, Line 1 replace "ethylene" with --ethyl--.
(PTO ERROR)

Signed and Sealed this

Twelfth Day of May, 1992

*Attest:*

DOUGLAS B. COMER

*Attesting Officer*     *Acting Commissioner of Patents and Trademarks*